(12) United States Patent
Zhang et al.

(10) Patent No.: US 10,107,056 B2
(45) Date of Patent: Oct. 23, 2018

(54) CORE HOLDING SYSTEM

(71) Applicant: PetroChina Company Limited, Beijing (CN)

(72) Inventors: Yapu Zhang, Beijing (CN); Zhengming Yang, Beijing (CN); Xuewei Liu, Beijing (CN); Haitao Hou, Beijing (CN); Yutian Luo, Beijing (CN); Shengchun Xiong, Beijing (CN); Ying He, Beijing (CN)

(73) Assignee: PetroChina Company Limited, Beijing (CN)

( * ) Notice: Subject to any disclaimer, the term of this patent is extended or adjusted under 35 U.S.C. 154(b) by 76 days.

(21) Appl. No.: 15/486,936

(22) Filed: Apr. 13, 2017

(65) Prior Publication Data

US 2018/0088012 A1    Mar. 29, 2018

(30) Foreign Application Priority Data

Sep. 29, 2016 (CN) .......................... 2016 1 0865102
Nov. 24, 2016 (CN) .......................... 2016 1 1050036

(51) Int. Cl.
*E21B 25/10*    (2006.01)
*G01N 1/44*    (2006.01)
(Continued)

(52) U.S. Cl.
CPC .............. *E21B 25/10* (2013.01); *E21B 25/14* (2013.01); *E21B 49/02* (2013.01); *G01N 1/44* (2013.01); *E21B 41/00* (2013.01); *G01N 33/24* (2013.01)

(58) Field of Classification Search
CPC ............ G01N 1/44; G01N 33/24; G01N 1/04; G01N 1/08; E21B 49/02; E21B 25/10; E21B 25/06; E21B 25/005; E21B 25/14
See application file for complete search history.

(56) References Cited

U.S. PATENT DOCUMENTS 4,304,122 A * 12/1981 Tentor ................ G01N 15/0826
73/152.07

FOREIGN PATENT DOCUMENTS

CN        102419363 A        4/2012
CN        102707033 A        10/2012
(Continued)

*Primary Examiner* — Paul M. West
(74) *Attorney, Agent, or Firm* — Hamilton, Brook, Smith & Reynolds, P.C.

(57) ABSTRACT

The present disclosure discloses a core holding system, comprising: a sleeve in which a cavity capable of accommodating a core is formed; an adjustment plug set comprising a plurality of adjustment plugs having grooves of different diameters, wherein any one of the adjustment plugs is dismountably connectable to the sleeve, and when the adjustment plug is mounted on the sleeve, an end of the adjustment plug having the groove is insertable into the sleeve while abutting against the core; a heating module provided to sheathe the sleeve; and a thermal insulation module provided to sheathe the heating module. Before the core is held, the operator may select a matched adjustment plug from the adjustment plug set according to a diameter of a core to be held, so that a diameter of the groove of the adjustment plug is matched with a diameter of an end of the core, thereby ensuring that the end of the core can be engaged in the groove, thus ensuring that the core holding system can stably and tightly engage the core, and preventing the held core from being shifted or loosened.

15 Claims, 4 Drawing Sheets

(51) Int. Cl.
*E21B 25/14* (2006.01)
*E21B 49/02* (2006.01)
*E21B 41/00* (2006.01)
*G01N 33/24* (2006.01)

(56) References Cited

FOREIGN PATENT DOCUMENTS

| | | |
|---|---|---|
| CN | 104267174 A | 1/2015 |
| CN | 204203214 A | 3/2015 |
| CN | 104792971 A | 7/2015 |
| CN | 105223122 A | 1/2016 |
| JP | 2001-207771 A | 8/2001 |

* cited by examiner

CORE HOLDING SYSTEM

RELATED APPLICATIONS

This application claims priority under 35 U.S.C. § 119 or 365 to Chinese Patent Application No. 201610865102.9, filed on Sep. 29, 2016 and Chinese Patent Application No. 201611050036.6, filed on Nov. 24, 2016. The entire teachings of the above applications are incorporated herein by reference.

TECHNICAL FIELD

The present disclosure relates to the field of geological exploration, and particularly, to a core holding system.

BACKGROUND ART

In the field of petroleum development, geological exploration, etc., a core holding system shall be used in the laboratories to hold cores drilled from stratums of a region to be researched. In the prior art, the core holding system has the standard sizes of 25 mm, 38 mm, 100 mm, etc. But in the actual coring process, the cores drilled from the stratums may not completely meet the standard sizes of the core holding system in the prior art, due to the reasons of the equipment or the personnel operations. The core diameter may be larger or smaller than the standard size of the core holding system, thus some of the cores cannot be held by the core holding system. The core drilling usually costs a lot of manpower and material resources. Therefore, it is a problem to be urgently solved to ensure that all of the cores drilled from the stratums can satisfy the usage by the core holding system.

In addition, when the cores are to be tested or researched, they shall be placed under the high temperature condition of the simulation stratum, which requires the holder that holds the cores to be placeable into the constant-temperature equipment. But the core holding system in the prior art has a large volume and cannot be placed into the constant-temperature equipment.

SUMMARY OF THE DISCLOSURE

In view of the above problems, an objective of the present disclosure is to provide a core holding system which produces a better effect.

In order to achieve the above objective, the present disclosure provides a core holding system, comprising:

a sleeve in which a cavity capable of accommodating a core is formed;

an adjustment plug set comprising a plurality of adjustment plugs having grooves of different diameters, wherein any one of the adjustment plugs is dismountably connectable to the sleeve, and when the adjustment plug is connected to the sleeve, an end of the adjustment plug having the groove is insertable into the sleeve while abutting against the core;

a heating module provided to sheathe the sleeve; and a thermal insulation module provided to sheathe the heating module.

Further, the core holding system selects an adaptive adjustment plug according to a diameter of a core to be held.

Further, the core holding system comprises a bracket on which the sleeve is rotatably provided around a first axis.

Further, a support is transversely and rotatably provided between the sleeve and the bracket, and a length direction of the support coincides with the first axis.

Further, there are two supports provided symmetrically.

Further, the bracket is provided with rollers enabling the bracket to slide relative to the ground.

Further, the adjustment plugs are provided at two ends of the sleeve, respectively, an end of the adjustment plug having the groove is insertable into the sleeve while abutting against the core, and the groove is tightly engageable with an end of the core.

Further, an end of the sleeve is provided with a stopper capable of securely disposing the adjustment plug, one end of the adjustment plug abutting against the core, and the other end of the adjustment plug abutting against the stopper.

Further, a diameter of the end of the adjustment plug abutting against the core is larger than a diameter of the other end of the adjustment plug, and the other end of the adjustment plug is capable of extending into a through hole formed in the stopper.

Further, the stopper comprises a body secured to the sleeve and formed with a threaded hole matched with an inner diameter of the sleeve, and a threaded member dismountably in a threaded connection with the threaded hole, the through hole being provided in the threaded member.

Further, the thermal insulation module comprises a thermal insulation ring that sheathes the sleeve and a thermal insulation cover that covers both ends of the sleeve.

Further, the adjustment plug set comprises a plurality of the adjustment plugs in which the grooves have the diameters of 100 mm, 101 mm, 103 mm, 105 mm, 107 mm, 109 mm and 110 mm, respectively.

Before the core is held, the operator may select a matched adjustment plug from the adjustment plug set according to a diameter of a core to be held, so that the diameter of the groove of the adjustment plug is matched with a diameter of an end of the core, thereby ensuring that the end of the core can be engaged in the groove, thus ensuring that the core holding system can stably and tightly engage the core, and preventing the held core from being shifted or loosened. In which, the adjustment plug set may comprise a plurality of grooves having different diameters, so that the core holding system is adaptive to the cores of different sizes, thereby ensuring that the drilled cores of different sizes can satisfy the usage by the core holding system.

In addition, the core holding system is further provided with a heating module and a thermal insulation module. The heating module may heat the sleeve of the core holding system, so that the core holding system can directly simulate a high temperature environment in the sleeve, thereby solving the problem that the core holding system has a large volume and cannot be placed into the constant-temperature and constant-pressure equipment.

1: sleeve; 11: cavity; 21: adjustment plug; 211: groove; 31: heating module; 32: thermal insulation module; 4: bracket; 41: stand pole; 42: roller; 5: support; 6: stopper; 61: through hole; 62: threaded member; A: core sample.

DETAILED DESCRIPTION OF THE PREFERRED EMBODIMENTS

In order that a person skilled in the art better understands the technical solutions in the present application, they will be clearly and completely described as follows with reference to the drawings of the embodiments of the present disclosure. Obviously, those described herein are just parts of the embodiments of the present disclosure rather than all of the embodiments. Based on the embodiments of the present disclosure, any other embodiment obtained by a person skilled in the art without paying any creative effort shall fall within the protection scope of the present disclosure.

In the drilling and coring process, due to the reasons of the equipment or the personnel operations, the full-diameter core samples drilled from the reservoir usually do not have regular outer diameters of 100 mm (the standard size of the core holding system is 100 mm), while most of the samples have outer diameters more than 100 mm, thus the caliber tolerance of the conventional full-diameter core holding system is limited, and the scientific research and detection of the precious core samples in many important stratums cannot be carried out. For example, the 25 mm and 38 mm core samples are obtained by being machined on an indoor drilling and cutting machine, and the size error is very small; while the full-diameter cores more than 100 mm are samples directly obtained in the drilling process, and their sizes cannot be standard. Thus the problem of irregular size cannot be avoided when the full-diameter cores are used for scientific researches.

Figure 1:
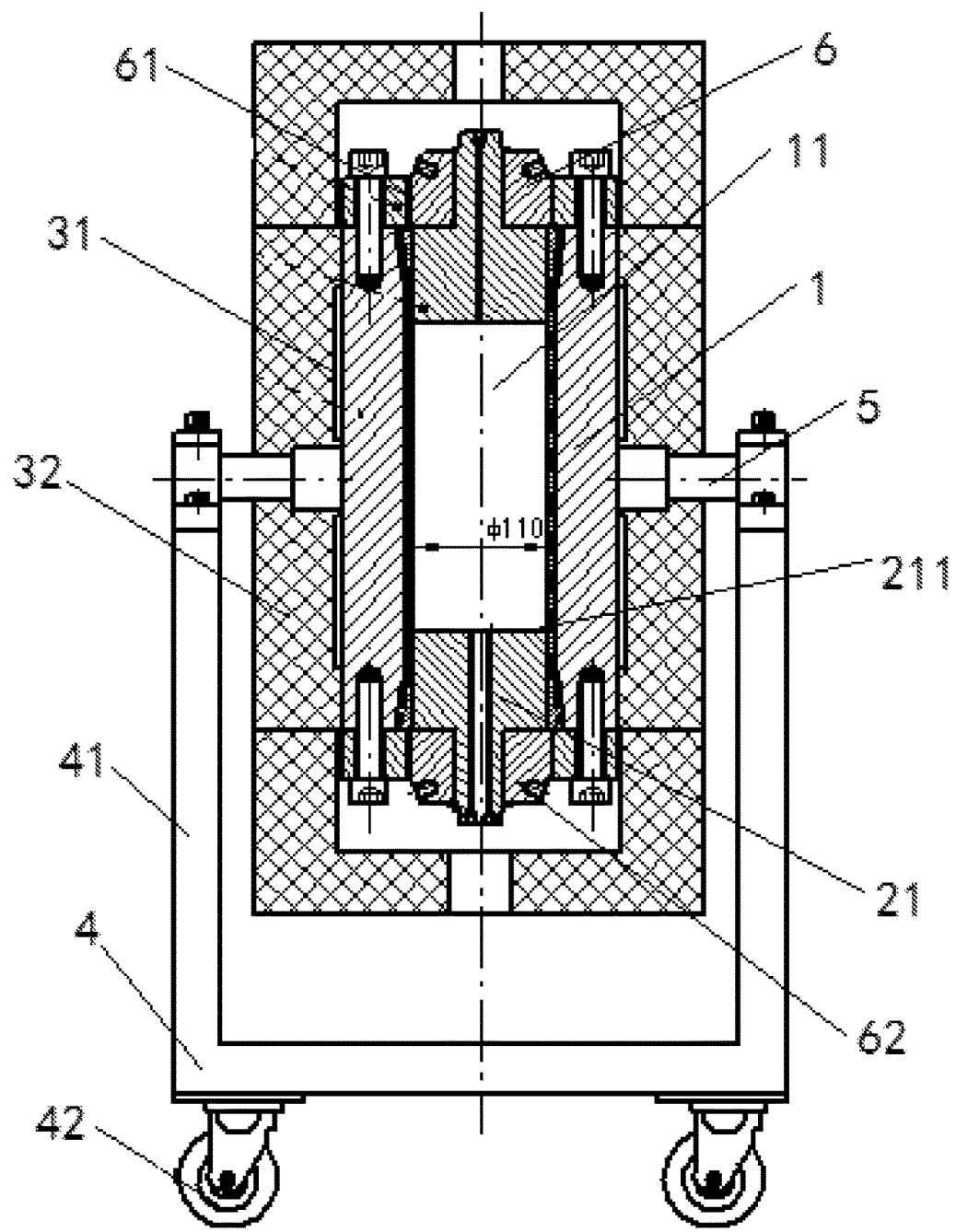
FIG. 1 is a structure diagram of a core holder in which an adjustment plug having a diameter of 110 mm is provided in a sleeve according to an embodiment of the present disclosure.

The present disclosure discloses a core holding system. As illustrated in FIG. 1, the core holding system comprises a sleeve 1 in which a cavity 11 capable of accommodating a core sample A is formed; an adjustment plug set comprising a plurality of adjustment plugs 21, one ends of which are formed with grooves 211 of different diameters, wherein any one of the adjustment plugs 21 is securely connectable to one end of the sleeve 1, and the end of the adjustment plug 21 having the groove 211 is insertable into the sleeve 1 while abutting against the core sample A; a heating module 31 provided to sheathe the sleeve 1; and a thermal insulation module 32 provided to sheathe the heating module 31.

Figure 2:
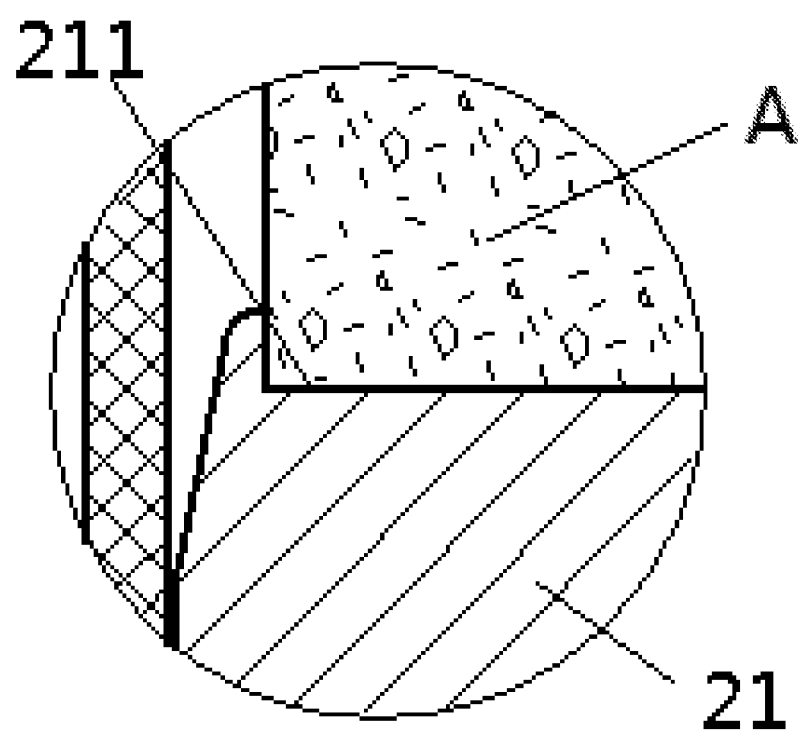
FIG. 2 is a local structure diagram of a core holder in which an adjustment plug having a diameter of 110 mm is provided in a sleeve according to an embodiment of the present disclosure.
Figure 4:
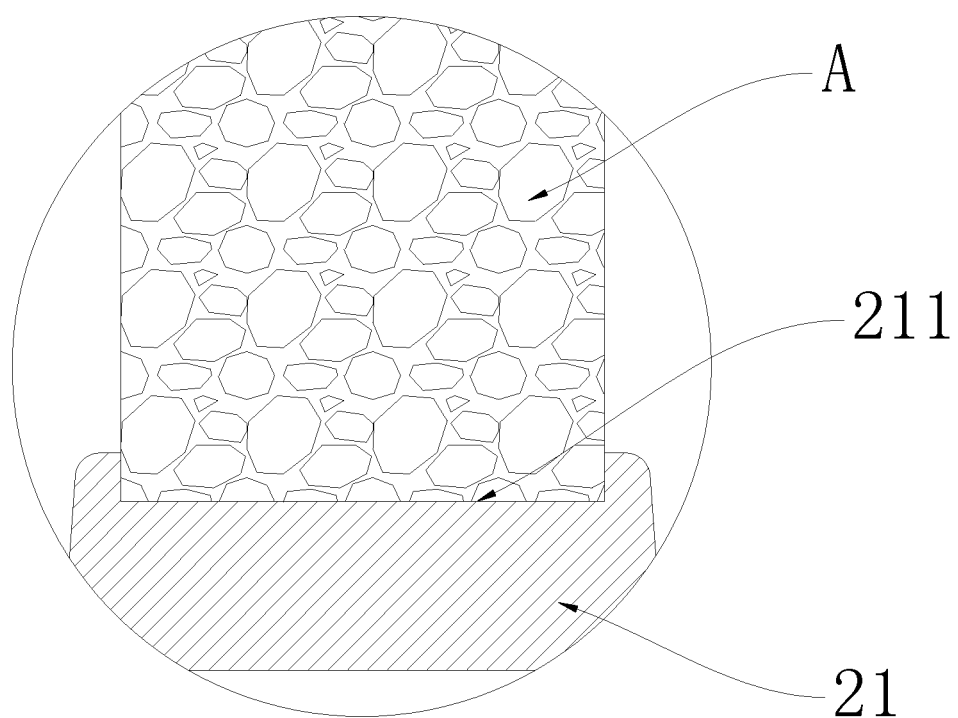
FIG. 4 is a local structure diagram of a core holder in which an adjustment plug having a diameter of 100 mm is provided in a sleeve according to an embodiment of the present disclosure.

Referring to FIGS. 2 and 4, which are local structure diagrams of an adjustment plug 21 having a groove 211. As illustrated in those figures, the groove 211 may form a limit groove having a circular cross section on the adjustment plug 21. When the core sample A is held by the core holding system, an end of the core sample A may abut against a bottom wall of the groove 211, and a side wall of the core sample A may abut against a side wall of the groove 211, so that the core sample A can be limited within the groove 211. The depth and diameter of the groove 211 can be determined depending on the core sample A actually to be held.

Before the core sample A is held, the operator may select a matched adjustment plug 21 from the adjustment plug set according to the diameter of the core sample A, so that the diameter of the groove 211 of the adjustment plug 21 is matched with the diameter of the end of the core sample A, thereby ensuring that the end of the core sample A can be engaged in the groove 211, thus ensuring that the holding system for the core sample A can stably and tightly engage the core sample A, and preventing the held core sample A from being shifted or loosened. In which, the adjustment plug set may comprise a plurality of grooves 211 having different diameters, so that the core holding system is adaptive to the cores of different sizes, thereby ensuring that the drilled cores can satisfy the usage by the core holding system.

In addition, the core holding system is further provided with a heating module 31 and a thermal insulation module 32. The heating module 31 can heat the sleeve 1 of the core holding system, so that the core holding system can directly simulate a high temperature environment in the sleeve 1, thereby solving the problem that the core holding system has a large volume and cannot be placed into the constant-temperature and constant-pressure equipment.

In this embodiment, the sleeve 1 may be a barrel with both ends opened. The barrel includes a cylindrical cavity 11 therein, and the diameter of the cylindrical cavity 11 is larger than the maximum diameter of the core sample A to be held, so that the core holding system can satisfy most of the cores having different diameters.

In this embodiment, the adjustment plug set may be a combination of a plurality of adjustment plugs 21 which can be provided separately. Before the use, the operator may select an adjustment plug 21 adaptive to the core sample A to be held. In a preferred embodiment, the plurality of adjustment plugs 21 may be provided separately, so that the operator can randomly select a certain adjustment plug 21. In another preferred embodiment, the plurality of adjustment plugs 21 may also be provided on a body together. The operator can adjust the position of the adjustment plug 21 on the body or rotate the adjustment plug 21, so that the adjustment plug 21 to be used is located at a mounting position. The specific structure of the adjustment plug set is not restricted in the present disclosure, provided that a proper adjustment plug 21 can be selected according to the diameter of the core sample A before the core sample A is held.

Figure 3:
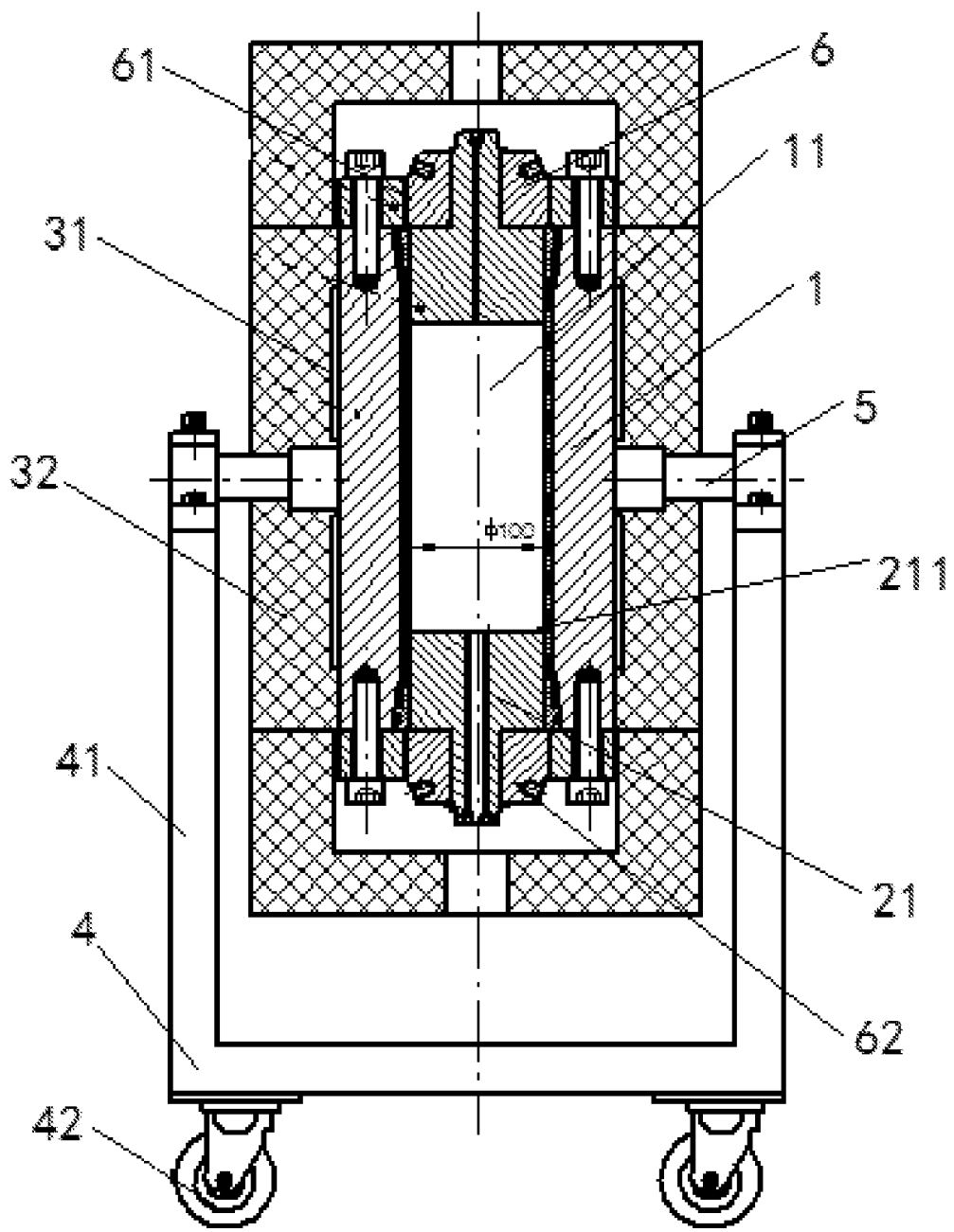
FIG. 3 is a structure diagram of a core holder in which an adjustment plug having a diameter of 100 mm is provided in a sleeve according to an embodiment of the present disclosure.

In a preferred embodiment, as illustrated in FIGS. 1 and 3, the adjustment plug set may comprise a plurality of adjustment plugs 21 in which the grooves 211 have the diameters of 100 mm, 101 mm, 103 mm, 105 mm, 107 mm, 109 mm and 110 mm, respectively, so as to adapt the core samples A of different diameters.

In this embodiment, the heating module 31 heats the sleeve 1, so that a high temperature chamber environment is formed in the sleeve 1. Specifically, the heating module 31 may be a heating resistance wire or a heating tile. The sleeve 1 may be sheathed by a plurality of resistance wires or heating tiles, or a whole piece of resistance wire or heating tile. The heating module 31 may be directly adhered to an outer sidewall of the sleeve 1 tightly to avoid any gap between the heating module 31 and the outer sidewall of the sleeve 1, thereby ensuring that the heating module 31 can effectively heating the chamber in the sleeve 1.

The thermal insulation module 32 may be provided to sheathe the heating module 31 for a thermal insulation of the sleeve 1, so that a high temperature environment can be formed in the sleeve 1.

In another preferred embodiment, the thermal insulation module 32 may comprise a thermal insulation ring that sheathes the sleeve 1 and a thermal insulation cover that covers both ends of the sleeve 1, so that the thermal insulation module 32 provides a good thermal insulation effect for the sleeve 1. In which, the thermal insulation material of the thermal insulation module 32 may be any one of polyester foam, asbestos, expanded perlite, mineral wool, glass wool and foamed plastics.

In this embodiment, the core holding system may comprise a bracket 4 on which the sleeve 1 is rotatably provided around a first axis. During the actual usage of the core holding system, since the core sample A is heavy, it is uneasy to mount the core sample A into the core holding system or dismount the core sample A from the core holding system. The sleeve 1 is rotatably provided to sheathe the bracket 4, so that when the core sample A is to be dismounted from the core holding system, the adjustment plug 21 at one end may be firstly dismounted from the sleeve 1, and then the sleeve 1 is rotated to be inclined for an angle, thus the core sample A can be slowly poured out of the sleeve 1.

Preferably, the support 5 may be transversely and rotatably provided between the sleeve 1 and the bracket 4, and the length direction of the support 5 coincides with the first axis. Specifically, the bracket 4 may comprise a base 43 and two symmetrical stand poles 41 vertically provided on the base 43. The support 5 may be provided between the stand pole 41 and the sleeve 1. The support 5 may be provided in the middle of the sleeve 1. The first axis is perpendicular to an axis of the length direction of the sleeve 1, so that the sleeve 1 is rotatable around the first axis. More preferably, there are two supports 5 provided symmetrically.

In another preferred embodiment, the bracket 4 may be provided with rollers 42 enabling the bracket 4 to slide relative to the ground, thereby facilitating the transport of the core holding system.

In a preferred embodiment, in order to more stably secure the core sample A within the core holding system, the adjustment plugs 21 may be provided at the two ends of the sleeve 1, respectively. An end of the adjustment plug 21 having the groove 211 is insertable into the sleeve 1 while abutting against the core sample A, and the groove 211 can be tightly engaged with the end of the core sample A. Specifically, the grooves 211 of the adjustment plugs 21 provided at both ends of the sleeve 1 may have the same or different diameters. The operator may select proper adjustment plugs 21 from the adjustment plug set according to the diameters of both ends of the actual core sample A, so that the grooves 211 of the adjustment plugs 21 at both ends can be tightly engaged with the ends of the core sample A.

In another preferred embodiment, the end of the sleeve 1 may be provided with a stopper 6 capable of securely disposing the adjustment plug 21. One end of the adjustment plug 21 abuts against the core sample A, while the other end of the adjustment plug 21 abuts against the stopper 6.

Specifically, the diameter of one end of the adjustment plug 21 that abuts against the core sample A may be larger than the diameter of the other end of the adjustment plug 21, and the other end of the adjustment plug 21 can extend into a through hole 61 formed in the stopper 6. Since the two ends of the adjustment plug 21 have different diameters, a transitive step may be formed on the adjustment plug 21. When the end having a smaller diameter extends into the through hole 61, the step surface of the step may abut against the bottom of the stopper 6, so as to limit the adjustment plug 21 at a fixed position.

In one preferred embodiment, the stopper 6 comprises a body secured to the sleeve 1, and a threaded hole matched with the inner diameter of the sleeve 1 is formed on the body. A threaded member 62 is dismountably in a threaded connection with the threaded hole, and the through hole 61 is provided in the threaded member 62. When the adjustment plug 21 is dismounted from the sleeve 1, the threaded member 62 may be directly dismounted from the body without needing to dismount the stopper 6 entirely from the sleeve 1, thereby facilitating the dismounting.

Before the core sample A is held by the core holding system, the diameters of both ends of the core sample A can be firstly determined. The operator determines the adjustment plugs 21 required at both ends of the sleeve 1 according to the acquired diameter of the core sample A. next, one end of an adjustment plug 21 having a groove 211 is inserted into one end of the sleeve 1, and then the stopper 6 is mounted outside the sleeve 1. Specifically, a threaded hole adaptive to the diameter of the adjustment plug 21 is formed in the stopper 6, so that when an adjustment plug 21 is dismounted from the sleeve 1 or replaced by other adjustment plug 21, the threaded member 62 provided in the threaded hole can be directly dismounted, and then the adjustment plug 21 is taken out or replaced.

After the adjustment plug 21 is mounted at one end, the sleeve 1 is rotatable around the first axis, so that the sleeve 1 forms a certain angle with the ground, and then the core sample A is slowly placed into the sleeve 1. When the core sample A is placed into the sleeve 1, one end of the core sample A abuts against the adjustment plug 21 having been provided in the sleeve 1, and then the other adjustment plug 21 is mounted. The sleeve 1 on one side of the adjustment plug 21 may also be provided with the stopper 6. After the core sample A is mounted on the core holding system, the heating module 31 may be turned on to heat the sleeve 1 of the core holding system, thereby forming an appropriate high temperature environment within the sleeve 1.

In December 2014, our laboratory received a batch of full-diameter core samples from a certain oil field in Iraq, and they require a detection of the gas log permeability. It is measured that the diameters of most of the cores exceed 100 mm, and those cores cannot be placed into the original core holding system. The transport of the full-diameter core samples from abroad to domestic costs a lot of manpower and material resources. In addition, the samples are very precious, and also crucially important to the reservoir evaluation of that oil field in Iraq. By using the core holding system of the present disclosure, the above test difficulty is successfully solved, and the detection of the gas log permeability is smoothly completed. Currently, the set of equipment is used to perform the water displacing oil detection for the full-diameter cores. Table 1 is a log sheet showing the detection made by using the core holding system.

TABLE 1

Original Log Sheet of Gas Log Permeability of Cores
Detection date: May 2015

| Core No. | Length/cm | Diameter/cm | Gas drive pressure/Mpa | Flow rate/ml · min$^{-1}$ | Gas log permeability/mD | Average gas log permeability/mD |
|---|---|---|---|---|---|---|
| 1 | 18.4 | 10.003 | 0.008 | 187.9 | 156.875 | 132.712 |
|   | 18.4 | 10.003 | 0.018 | 368.1 | 130.321 |  |
|   | 18.4 | 10.003 | 0.028 | 509.8 | 110.939 |  |
| 2 | 19.8 | 10.024 | 0.013 | 282.6 | 151.934 | 133.400 |
|   | 19.9 | 10.025 | 0.018 | 348.3 | 132.779 |  |
|   | 19.10 | 10.026 | 0.028 | 513.6 | 115.487 |  |
| 3 | 18.1 | 10.034 | 0.003 | 100.6 | 224.353 | 150.924 |
|   | 18.1 | 10.034 | 0.008 | 166.4 | 135.816 |  |
|   | 18.1 | 10.034 | 0.023 | 349.7 | 92.601 |  |
| 4 | 16.7 | 10.054 | 0.016 | 165.4 | 59.734 | 57.780 |
|   | 16.7 | 10.054 | 0.023 | 234.9 | 57.162 |  |
|   | 16.7 | 10.054 | 0.036 | 384.2 | 56.442 |  |
| 5 | 15.3 | 10.002 | 0.020 | 177.3 | 46.558 | 39.981 |
|   | 15.3 | 10.002 | 0.041 | 335.4 | 39.219 |  |
|   | 15.3 | 10.002 | 0.058 | 442.5 | 34.167 |  |
| 6 | 19.8 | 10.134 | 0.003 | 89.2 | 213.340 | 164.978 |
|   | 19.8 | 10.134 | 0.008 | 179.6 | 157.209 |  |
|   | 19.8 | 10.134 | 0.018 | 335.1 | 124.386 |  |
| 7 | 20.1 | 10.146 | 0.016 | 260.5 | 111.189 | 105.829 |
|   | 20.1 | 10.146 | 0.023 | 372.5 | 107.133 |  |
|   | 20.1 | 10.146 | 0.033 | 516.9 | 99.166 |  |
| 8 | 14.156 | 10.079 | 0.016 | 272.4 | 82.978 | 77.657 |
|   | 14.156 | 10.079 | 0.023 | 369.2 | 75.780 |  |
|   | 14.156 | 10.079 | 0.031 | 504.8 | 74.212 |  |

Note:
The confining pressure detected in the experiment is 3 MPa

It shall be appreciated that the above descriptions are made just for illustration rather than limitation. By reading the above descriptions, many embodiments and applications besides the provided examples will be apparent to a person skilled in the art. Thus, the range of the teachings shall not be determined with reference to the above descriptions, but all of the ranges of the appended claims and their owned equivalents. For the purpose of comprehensiveness, all of the articles and references, including the disclosures of the patent applications and publications, are incorporated herein by reference. The omission of any aspect of a subject matter disclosed herein in the claims does not intend to give up the content of the subject matter, and it shall not be deemed that the inventor does not consider the subject matter as a part of the disclosed subject matter of the invention.

What is claimed is:

1. A core holding system, comprising:
   a sleeve in which a cavity capable of accommodating a core is formed;
   an adjustment plug set comprising a plurality of adjustment plugs having grooves of different diameters, wherein any one of the adjustment plugs is dismountably connectable to the sleeve, and when the adjustment plug is connected to the sleeve, an end of the adjustment plug having the groove is insertable into the sleeve while abutting against the core;
   a heating module provided to sheathe the sleeve; and
   a thermal insulation module provided to sheathe the heating module.

2. The core holding system according to claim 1, wherein the core holding system selects an adaptive adjustment plug according to a diameter of a core to be held.

3. The core holding system according to claim 1, wherein the core holding system comprises a bracket on which the sleeve is rotatably provided around a first axis.

4. The core holding system according to claim 3, wherein a support is transversely and rotatably provided between the sleeve and the bracket, and a length direction of the support coincides with the first axis.

5. The core holding system according to claim 4, wherein there are two supports provided symmetrically.

6. The core holding system according to claim 3, wherein the bracket is provided with rollers enabling the bracket to slide relative to the ground.

7. The core holding system according to claim 1, wherein the adjustment plugs are provided at two ends of the sleeve, respectively, an end of the adjustment plug having the groove is insertable into the sleeve while abutting against the core, and the groove is tightly engageable with an end of the core.

8. The core holding system according to claim 7, wherein an end of the sleeve is provided with a stopper capable of securely disposing the adjustment plug, one end of the adjustment plug abutting against the core, and the other end of the adjustment plug abutting against the stopper.

9. The core holding system according to claim 8, wherein a diameter of the end of the adjustment plug abutting against the core is larger than a diameter of the other end of the adjustment plug, and the other end of the adjustment plug is capable of extending into a through hole formed in the stopper.

10. The core holding system according to claim 9, wherein the stopper comprises a body secured to the sleeve and formed with a threaded hole matched with an inner diameter of the sleeve, and a threaded member dismountably in a threaded connection with the threaded hole, the through hole being provided in the threaded member.

11. The core holding system according to claim 1, wherein an end of the sleeve is provided with a stopper capable of securely disposing the adjustment plug, one end of the adjustment plug abutting against the core, and the other end of the adjustment plug abutting against the stopper.

12. The core holding system according to claim 11, wherein a diameter of the end of the adjustment plug abutting against the core is larger than a diameter of the other end of the adjustment plug, and the other end of the adjustment plug is capable of extending into a through hole formed in the stopper.

13. The core holding system according to claim 12, wherein the stopper comprises a body secured to the sleeve and formed with a threaded hole matched with an inner diameter of the sleeve, and a threaded member dismountably in a threaded connection with the threaded hole, the through hole being provided in the threaded member.

14. The core holding system according to claim 1, wherein the thermal insulation module comprises a thermal insulation ring that sheathes the sleeve and a thermal insulation cover that covers both ends of the sleeve.

15. The core holding system according to claim 1, wherein the adjustment plug set comprises a plurality of the adjustment plugs in which the grooves have the diameters of 100 mm, 101 mm, 103 mm, 105 mm, 107 mm, 109 mm and 110 mm, respectively.

* * * * *